US010675350B2

(12) United States Patent
Wu

(10) Patent No.: US 10,675,350 B2
(45) Date of Patent: Jun. 9, 2020

(54) NANOPARTICLES OF INDIRUBIN, DERIVATIVES THEREOF AND METHODS OF MAKING AND USING SAME

(71) Applicant: Phosphorex, Inc., Hopkinton, MA (US)

(72) Inventor: Bin Wu, Sharon, MA (US)

(73) Assignee: Phosphorex, Inc., Hopkinton, MA (US)

( * ) Notice: Subject to any disclaimer, the term of this patent is extended or adjusted under 35 U.S.C. 154(b) by 0 days.

(21) Appl. No.: 16/040,640

(22) Filed: Jul. 20, 2018

(65) Prior Publication Data

US 2019/0054174 A1 Feb. 21, 2019

Related U.S. Application Data

(60) Division of application No. 14/573,212, filed on Dec. 17, 2014, now Pat. No. 10,039,829, which is a continuation of application No. PCT/US2013/046981, filed on Jun. 21, 2013.

(60) Provisional application No. 61/662,469, filed on Jun. 21, 2012.

(51) Int. Cl.
*A61K 9/14* (2006.01)
*A61K 31/404* (2006.01)
*A61K 47/10* (2017.01)

(52) U.S. Cl.
CPC .............. *A61K 47/10* (2013.01); *A61K 9/14* (2013.01); *A61K 9/146* (2013.01); *A61K 31/404* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 4,929,242 A | 5/1990 | Desecki et al. | |
| 5,862,999 A * | 1/1999 | Czekai | A61K 9/146 24/184 |
| 10,039,829 B2* | 8/2018 | Wu | A61K 9/14 |
| 2004/0033267 A1 | 2/2004 | Merisko-Liversidge et al. | |
| 2004/0204434 A1 | 10/2004 | Shafer et al. | |
| 2004/0225002 A1* | 11/2004 | Wang | C07D 209/34 514/414 |
| 2006/0159628 A1 | 7/2006 | Liversidge et al. | |
| 2006/0159766 A1 | 7/2006 | Jenkins et al. | |
| 2006/0159767 A1 | 7/2006 | Jenkins et al. | |
| 2006/0165806 A1 | 7/2006 | Liversidge et al. | |
| 2006/0188566 A1* | 8/2006 | Liversidge | A61K 9/0019 424/451 |
| 2006/0193920 A1 | 8/2006 | Bosch et al. | |
| 2006/0204588 A1 | 9/2006 | Liversidge et al. | |
| 2006/0210639 A1 | 9/2006 | Liversidge et al. | |
| 2006/0216353 A1 | 9/2006 | Liversidge et al. | |
| 2006/0246142 A1 | 11/2006 | Liversidge et al. | |
| 2007/0155816 A1 | 7/2007 | Kim et al. | |
| 2008/0220074 A1 | 9/2008 | Bosch et al. | |
| 2009/0035366 A1 | 2/2009 | Liversidge et al. | |
| 2009/0274621 A1* | 11/2009 | Wegrzyn | A61K 47/54 424/1.65 |
| 2011/0064800 A1 | 3/2011 | Jenkins et al. | |

FOREIGN PATENT DOCUMENTS

| | | |
|---|---|---|
| CN | 1615852 A | 5/2005 |
| CN | 101362066 A | 2/2009 |
| CN | 101775082 A | 7/2010 |
| CN | 102018736 A | 4/2011 |
| CN | 102228433 A | 11/2011 |
| EP | 2111867 A1 | 10/2009 |
| EP | 2168964 A1 | 3/2010 |
| JP | 2007-522114 A | 8/2007 |
| JP | 2008-521931 A | 6/2008 |
| JP | 2008-545752 A | 12/2008 |
| JP | 2009-292810 A | 12/2009 |
| JP | 2010-529050 A | 8/2010 |
| JP | 2011-503044 A | 1/2011 |
| WO | 2002/0100401 A1 | 12/2002 |
| WO | 2003/0051900 A1 | 6/2003 |
| WO | 2005/069933 A2 | 8/2005 |
| WO | 2006/060698 A1 | 6/2006 |
| WO | 2006/130769 A2 | 12/2006 |
| WO | 2009/060226 A1 | 5/2009 |

OTHER PUBLICATIONS

SP Williams, MO Nowicki, F Liu, R Press, J Godlewski, M Abdel-Rasoul, B Kaur, SA Fernandez, EA Chiocca, SE Lawler. "Indirubins Decrease Glioma Invasion by Blocking Migratory Phenotypes in Both the Tumor and Stromal Endothelial Cell Compartments." Cancer Research, vol. 71(16), 5374-5380. (Year: 2011).*
P Kocbek, S Baumgartner, J Kristl. "Preparation and evaluation of nanosuspensions for enhancing the dissolution of poorly soluble drugs." International Journal of Pharmaceutics, vol. 312, 2006, pp. 179-186. (Year: 2006).*
E-K Shin, J-K Kim. "Indirubin derivative E804 inhibits angiogenesis." BMC Cancer, vol. 12:164, 2012, pp. 1-10, published May 3, 2012. (Year: 2012).*
Sigma-Aldrich. "Indirubin Derivative E804—CAS 854171-35-0—Calbiochenn." Accessed at https://www.sigmaaldrich.com/catalog/product/mm/402081?lang=en&region=US on Jan. 23, 2020, pp. 1-2. (Year: 2020).*
WebMD. https://www.webmd.com/cancer/lymphoma/cml-need-to-know-first?print=true accessed Jan. 23, 2020, pp. 1-5. (Year: 2020).*
Baskurt et al., Blood rheology and hemodynamics. Semin Thromb Hemost. Oct. 2003;29(5):435-50.
Jiang et al., Preparation and in vitro dissolution of polyvinylpyrrolidone solid dispersion containing indirubin. J Third Mil Med Univ. Mar. 2012;34(6):538-541, only abstract is in English.

(Continued)

*Primary Examiner* — Isaac Shomer
(74) *Attorney, Agent, or Firm* — McCarter & English, LLP; Yu Lu

(57) ABSTRACT

The disclosure provides nanoparticles of indirubin and methods of making and using these particles for the treatment of cancer, neurodegenerative disorders and inflammatory diseases. The effective average particle size of the nanoparticles is less than 2000 nm.

7 Claims, No Drawings

(56) References Cited

OTHER PUBLICATIONS

Kim et al., Antitumor activity of novel indirubin derivatives in rat tumor model. Clin Cancer Res. Jan. 1, 2007;13(1):253-9.
Williams et al., Indirubins decrease glioma invasion by blocking migratory phenotypes in both the tumor and stromal endothelial cell compartments. Cancer Res. Aug. 15, 2011;71(16):5374-80.
Yang, Clinical observation of 43 psoriasis patients treated with indirubin. Yunnan Traditional Chinese Medicine Journal Dec. 1982;2:21-22, Not in English.
Yun, Indirubin-3'oxime, IO in the function of neuron protection. PhD Thesis, pp. I-IV. Sep. 10, 2007, Not in English.
Includes Chinese Office Action for Application No. 201380043697.4, dated Mar. 8, 2017. 17 pages, Includes English translation.

* cited by examiner

NANOPARTICLES OF INDIRUBIN, DERIVATIVES THEREOF AND METHODS OF MAKING AND USING SAME

REFERENCE TO RELATED APPLICATION

This application is a divisional application of U.S. patent application Ser. No. 14/573,212, filed on Dec. 17, 2014, which is a continuation of International Patent Application No. PCT/US2013/046981, filed on Jun. 21, 2013, which claims the benefit of the filing date of U.S. Provisional Application No. 61/662,469, filed on Jun. 21, 2012, the entire contents of each of the above applications are incorporated herein by reference.

BACKGROUND OF THE INVENTION

Indirubin is extracted from the indigo plant. Indirubin is a constituent of a traditional Chinese herbal formula, Dang Gui Long Hui Wan used in the treatment of chronic myelogenous leukemia (CML). It has also been used in Asia as a systemic treatment for psoriasis.

In vitro and animal studies of indirubin have indicated anti-inflammatory, antitumor and neuroprotective effects of indirubin. Recently researchers discovered that indirubin both blocks the migration of glioblastoma cells, preventing their spread to other areas of the brain, and the migration of endothelial cells, preventing them from forming the new blood vessels that the tumor needs to grow. Glioblastomas occur in about 18,500 Americans annually and kill nearly 13,000 of them. Glioblastoma multiforme is the most common and lethal form of the malignancy, with an average survival of 15 months after diagnosis.

Indirubin also inhibits cyclin-dependent kinases in tumor cells. A derivative of indirubin was shown to enhance the cytotoxic effects of adriamycin. A small clinical study of indirubin in patients with head and neck cancer found a reduction in mucosal damage from radiation therapy. Meisoindigo, a metabolite of indirubin, has also been shown to have similar properties. Positive effects following long term use of indirubin for the treatment of CML have been reported.

The findings suggest that indirubin simultaneously targets tumor invasion and angiogenesis and that drugs of the indirubin family may improve survival in glioblastoma.

However, indirubin has a poor aqueous solubility and poor permeability, which limit its bioavailability, efficacy and delivery. Therefore, there exists a need in the art for indirubin formulations that can increase solubility, bioavailability, improve clinical efficacy, reduce patient dose variation, and potentially reduce side effects.

SUMMARY OF THE INVENTION

The present disclosure provides a nanoparticulate indirubin composition, or derivatives thereof, including particles of indirubin, or derivatives or salts thereof, wherein the indirubin particles have an effective average particle size of less than 2 microns; and at least one surface stabilizer. In certain embodiments, the effective average particle size of the nanoparticulate indirubin particles can be less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 140 nm, less than 130 nm, less than 120 nm, less than 110 nm, less than 100 nm, less than 90 nm, less than 80 nm, less than 70 nm, less than 60 nm, or less than 50 nm. In certain specific embodiments, the effective average particle size of the nanoparticulate indirubin particles is less than 1000 nm or 500 nm.

In other embodiments, at least about 70%, at least about 90%, at least about 95%, or at least about 99% of the indirubin particles have a particle size less than the effective average particle size. Preferably, at least about 70% of the indirubin particles have a particle size less than the effective average particle size. In some embodiments, the composition is formulated for administration by oral, pulmonary, rectal, ophthalmic, colonic, parenteral, intracisternal, intravaginal, intraperitoneal, local, buccal, nasal, or topical administration. In one embodiment, the composition is formulated for oral administration. In another embodiment, the composition is formulated for intravenous administration. In certain embodiments, the composition further comprises one or more pharmaceutically acceptable excipients, carriers, or a combination thereof.

In other embodiments, the indirubin is present in an amount selected from the group consisting of from about 99.5% to about 0.001%, from about 95% to about 0.1%, and from about 90% to about 0.5%, by weight, based on the total combined dry weight of the indirubin and at least one surface stabilizer, not including other excipients. In one embodiment, the indirubin is present from about 80% to about 99.9999%, by weight, based on the total combined dry weight of the indirubin and at least one surface stabilizer, not including other excipients.

In another embodiment, the at least one surface stabilizer is present in an amount selected from about 0.5% to about 99.999%, from about 5.0% to about 99.9%, and from about 10% to about 99.5%, by weight, based on the total combined dry weight of the indirubin and at least one surface stabilizer, not including other excipients. In one embodiment, the at least one surface stabilizer is present in an amount of from about 0.0001% to about 20% by weight, based on the total combined dry weight of the indirubin and at least one surface stabilizer, not including other excipients. In another embodiment, the composition includes at least two surface stabilizers.

In another embodiment, the surface stabilizer is selected from an anionic surface stabilizer, a cationic surface stabilizer, a zwitterionic surface stabilizer, and an ionic surface stabilizer. The at least one surface stabilizer can be selected from cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oils, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethylcellulose phthalate, noncrystalline cellulose, magnesium aluminum silicate, triethanolamine, polyvinyl alcohol, polyvinylpyrrolidone, 4-(1,1,3,3-tetranlethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly- (glycidol), decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, lysozyme, PEG-derivatized phospholipid, PEG-derivatized cholesterols, PEG-3 derivatized vitamin A, PEG-derivatized vitamin E, and random copolymers of vinyl acetate and vinyl pyrrolidone. In one embodiment, the at least one surface stabilizer is a poloxamer. The poloxamer can be block copolymers of ethylene oxide and propylene oxide. In certain embodiments, the poloxamer is a block co-polymer of ethylene oxide (Pluronic F-68®).

In other embodiments, the at least one cationic surface stabilizer is selected from a polymer, a biopolymer, a polysaccharide, a cellulosic, an alginate, a nonpolymeric compound, a phospholipid, zwitterionic stabilizers, poly-n-methylpyridinium, anthryul pyridinium chloride, chitosan, polylysine, polyvinylimidazole, polybrene, polymethylmethacrylate trimethylammoniumbromide bromide (PMlMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol) 2000] (sodium salt), Poly(2-methacryloxyethyl trimethylammonium bromide), poloxamines, lysozyme, alginic acid, carrageenan, POLYOX, cationic lipids, sulfonium, phosphonium, quarternary ammonium compounds, stearyltrimethylammonium chloride, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium bromide, $C_{12-15}$dimethyl hydroxyethyl ammonium chloride, $C_{12-15}$dimethyl hydroxyethyl ammonium bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$) dimethylbenzyl ammonium chloride, N-alkyl ($C_{14-18}$)dimethyl-benzyl ammonium chloride, N-tetradecyldimethylbenzyl ammonium chloride monohydrate, dimethyl didecyl ammonium chloride, N-alkyl and ($C_{12-18}$) dimethyl-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl I-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride, dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, polyquaternium 10, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, quaternized ammonium salt polymers, alkyl pyridinium salts, amines, protonated quaternary acrylamides, methylated quaternary polymers, and cationic guar.

In other embodiments, the amine is selected from the group consisting of alkylamines, dialkylamines, alkanolamines, polyethylenepolyamines, N,Ndialkylaminoalkyl acrylates, vinyl pyridine, amine salts, lauryl amine acetate, stearyl amine acetate, alkylpyridinium salt, alkylimidazolium salt, amine oxides, and, imide azolinium salts.

In other embodiments, the cationic surface stabilizer is a nonpolymeric compound selected from the group consisting of benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, behenalkonium chloride, benzethonium chloride, cetylpyridinium chloride, behentrimonium chloride, lauralkonium chloride, cetalkonium chloride, cetrimonium bromide, cetrimonium chloride, cethylamine hydro fluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquatemium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

In other embodiments, the composition includes hypromellose, docusate sodium, or a combination thereof as surface stabilizers.

In other embodiments, the composition further includes an indirubin composition having an effective average particle size of greater than 2 microns. The composition can also include at least one additional nanoparticulate indirubin composition having an effective average particle size of less than 2 microns, wherein said additional nanoparticulate indirubin composition has an effective average particle size which is different than the effective average particle size of the nanoparticulate indirubin composition.

In another embodiment, the composition also includes at least one nonindirubin active agent. The active agent can be selected from amino acids, proteins, peptides, nucleotides, anti-obesity drugs, nutraceuticals, dietary supplements, central nervous symptom stimulants, carotenoids, corticosteroids, elastase inhibitors, anti-fungals, alkylxanthine, oncology therapies, anti-emetics, analgesics, opioids, antipyretics, cardiovascular agents, anti-inflammatory agents, anthelmintics, antianhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, alpha-adrenergic receptor blocking agents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants, anoretics, sympathomimetics, thyroid agents, vasodilators, vasomodulator, xanthines, Mu receptor antagonists, Kappa receptor antagonists, non-narcotic analgesics, monoamine uptake inhibitors, adenosine regulating agents, cannabinoids, Substance P antagonists, neurokinin-1 receptor antagonists, and sodium channel blockers. The nutraceutical can be selected from lutein, folic acid, fatty acids, fruit extracts, vegetable extracts, vitamin supplements, mineral supplements, phosphatidylserine, lipoic acid, melatonin, glucosanline/chondroitin, Aloe Vera, Guggul, glutamine, amino acids, green tea, lycopene, whole foods, food additives, herbs, phytonutrients, antioxidants, flavonoid constituents of fruits, evening primrose oil, flax seeds, fish oils, marine animal oils, and probiotics.

In certain embodiments, the at least one non-indirubin active agent has an effective average particle size of less than or greater than 2 microns.

In other embodiments, the composition is formulated into a liquid dosage form, wherein the dosage form has a viscosity of less than 2000 mPas at a shear rate of 0.1 (l/s). The viscosity at a shear rate of 0.1 (l/s) can be selected from about 2000 mPas to about 1 mPas, from about 1900 mPas to about 1 mPas, from about 1800 mPas to about 1 mPs, from about 1700 mPas to about 1 mPas, from about 1600 mPas to about 1 mPs, from about 1500 mPas to about 1 mPas, from about 1400 mPas to about 1 mPs, from about 1300 mPs to about 1 mPas, from about 1200 mPs to about 1 mPas, from about 1100 mPas to about 1 mPas, from about 1000 mPas to about 1 mPas, from about 900 mPas to about 1 mPas, from about 800 mPas to about 1 mPas, from about 700 mPas to about 1 mPas, from about 600 mPas to about 1 mPs, from about 500 mPas to about 1 mPas, from about 400 mPas to about 1 mPas, from about 300 mPas to about 1 mPas, from about 200 mPas to about 1 mPas, from about 175 mPas to about 1 mPs, from about 150 mPas to about 1 mPs, from about 125 mPas to about 1 mPas, from about 100 mPas to about 1 mPas, from about 75 mPs to about 1 mPas, from about 50 mPas to about 1 mPas, from about 25 mPas to about 1 mPas, from about 15 mPas to about 1 mPas, from about 10 mPs to about 1 mPas, and from about 5 mPas to about 1 mPas.

In certain embodiments, the viscosity of the dosage form is selected from the group consisting of less than $\frac{1}{200}$, less than $\frac{1}{100}$, less than $\frac{1}{50}$, less than $\frac{1}{25}$, and less than $\frac{1}{10}$ of the viscosity of a liquid dosage form of a conventional non-nanoparticulate indirubin composition, at the same concentration per ml of indirubin. The viscosity of the dosage form can also be selected from less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, and less than 90% of the viscosity of a liquid dosage form of a conventional non-nanoparticulate indirubin composition at the same concentration per ml of indirubin. The amount of indirubin per ml in the liquid dosage form can be equal to or greater than the amount of indirubin per ml of a liquid dosage form of a conventional non-nanoparticulate indirubin composition.

In certain embodiments, upon administration the composition redisperses such that the indirubin particles have an effective average particle size selected from the group consisting of less than 2 microns, less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 100 nm, less than 75 nm, and less than 50 nm. In one embodiment, the average particle size can be less than 2 microns upon redispersion.

In other embodiments, the composition redisperses in a biorelevant media such that the indirubin particles have an effective average particle size selected from less than 2 microns, less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 100 nm, less than 75 nm, and less than 50 nm. In one embodiment, the average particle size can be less than 2 microns upon redispersion.

The certain embodiments, the therapeutically effective amount of indirubin is selected from the group consisting of 17, 20, 33, and 50% of the therapeutically effective amount of a conventional non-nanoparticulate indirubin composition. The nanoparticulate indirubin composition can also be formulated into a dosage form for oral administration, wherein the relative bioavailability of the nanoparticulate indirubin composition compared to a solution is selected from the group consisting of greater than 1%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, 80%, greater than 85%, greater than 90%, and greater than 95%. In one embodiment, the relative bioavailability of the nanoparticulate indirubin composition compared to a solution is selected from the group consisting of greater than 80%.

The present disclosure also provides a method of making the nanoparticulate indirubin composition described above including contacting indirubin particles with at least one surface stabilizer for a time and under conditions sufficient to provide a nanoparticulate indirubin composition having an effective average particle size of less than 2 microns. The contacting step can include grinding, wet grinding and/or homogenizing and emulsification. The contacting step can also include the steps of dissolving the indirubin particles in a solvent; adding the resulting indirubin solution to a solution comprising at least one surface stabilizer; and precipitating the solubilized indirubin and at least one surface by the addition thereto of a non-solvent.

The present disclosure also provides a method of treating cancer in a subject in need thereof with a nanoparticulate indirubin formulation described above. The cancer can be glioblastoma or leukemia. The subject can be a human. The present disclosure also provides a method of treating a neurodegenerative disorder in a subject in need thereof with a nanoparticulate indirubin formulation described above.

The neurodegenerative disorder can be Alzheimer's disease. The subject can be a human. The method can also include administering an agent that enhances the permeability of the blood brain barrier to the subject in need thereof.

The present disclosure also provides a method of treating an inflammatory disorder in a subject in need thereof with a nanoparticulate indirubin formulation described above. The inflammatory disorder can be psoriasis. The subject can be a human.

DETAILED DESCRIPTION OF THE INVENTION

The present disclosure is directed to nanoparticulate compositions comprising indirubin or derivatives thereof. The compositions comprise indirubin and at least one surface stabilizer that is preferably adsorbed on or associated with the surface of the drug. The nanoparticulate indirubin particles have an effective average particle size of less than about 2 microns, preferably less than 1 micron, and more preferably less than 500 nm.

The molecular structure of indirubin is shown below.

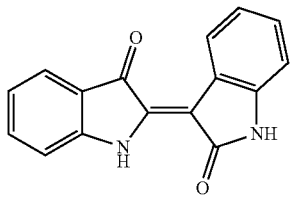 [SMILES: O=C1Nc2ccccc2/C1=C1/Nc2ccccc2C1=O]

Derivatives of indirubin include mesoindigo, indirubin 3' oximes (e.g., indirubin-3'-oxime, 5'-nitro-indirubinoxime, 5'-fluoro-indirubinoxirne, 5'-bromo-indirubin-3'-monoxime, 6'-bromo-indirubin-3'-monoxime, 7'-bromo-indirubin-3'-monoxime and 5'-trimethylacetamino-indirubinoxime), IDR-E804 (Shim et al., *BMC Cancer*, 12:164 (May 3, 2012), indirubin hydrazone derivatives.

As taught in U.S. Pat. No. 5,145,684, not every combination of surface stabilizer and active agent will result in a stable nanoparticulate composition. It was surprisingly discovered that stable nanoparticulate indirubin formulations can be made, and it was even more surprisingly discovered that stable nanoparticulate indirubin formulations having average particle size below 500 nm can be made.

The nanoparticle formulations described herein solve the insolubility problem of indirubin by processing indirubin into nanosized particles. The nanoparticle indirubin have increased solubility, bioavailability and delivery options.

The present disclosure uses several definitions, as set forth below and throughout the application.

As used herein, "about" will mean up to plus or minus 10% of the particular term.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein with reference to stable drug particles, "stable" includes, but is not limited to, one or more of the following parameters: (1) that the indirubin particles do not appreciably flocculate or agglomerate due to interparticle attractive forces, or otherwise significantly increase in particle size over time; (2) that the physical structure of the indirubin particles is not altered over time, such as by conversion from an amorphous phase to crystalline phase; (3) that the indirubin particles are chemically stable; and/or (4) where the indirubin has not been subject to a heating step at or above the melting point of the indirubin in the preparation of the nanoparticles described herein.

"Conventional active agents or drugs" refer to non-nanoparticulate compositions of active agents or solubilized active agents or drugs. Non-nanoparticulate active agents have an effective average particle size of greater than about 2 microns, meaning that at least 50% of the active agent particles have a size greater than about 2 microns. (Nanoparticulate active agents as defined herein have an effective average particle size of less than about 2 microns.)

"Therapeutically effective amount" as used herein with respect to a drug dosage, shall mean that dosage that provides the specific pharmacological response for which the drug is administered in a significant number of subjects in need of such treatment. It is emphasized that a "therapeutically effective amount" administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

Indirubin Compositions

The present disclosure provides compositions including nanoparticulate indirubin particles and at least one surface stabilizer. The surface stabilizers are preferably associated with the surface of the indirubin particles. Surface stabilizers useful herein do not chemically react with the indirubin particles or themselves. Preferably, individual molecules of the surface stabilizer are essentially free of intermolecular cross-linkages. The compositions can comprise two or more surface stabilizers.

The present disclosure also includes nanoparticulate indirubin compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration (in solid, liquid, or aerosol (i.e., pulmonary) form), vaginal, nasal, rectal, ocular, local (powders, creams, ointments or drops), buccal, intracisternal, intraperitoneal, topical administration, and the like.

1. Indirubin Nanoparticles

Indirubin may be used to treat a variety of diseases. These diseases include but are not limited to cancer including chronic myelogenous leukemia (CML) and glioblastomas, neurodegenerative disorders including Alzheimer's disease and inflammatory diseases including psoriasis.

2. Surface Stabilizers

The choice of a surface stabilizer for indirubin is non-trivial and required extensive experimentation to realize a desirable formulation. Accordingly, the present disclosure is directed to the surprising discovery that indirubin nanoparticulate compositions can be made.

Combinations of more than one surface stabilizer can be used in the compositions described herein. Useful surface stabilizers which can be employed in the compositions described herein include, but are not limited to, known organic and inorganic pharmaceutical excipients. Such excipients include various polymers, low molecular weight oligomers, natural products, and surfactants. Surface stabilizers include nonionic, cationic, zwitterionic, and ionic surfactants.

Representative examples of other useful surface stabilizers include hydroxypropyl methylcellulose, hydroxypropylcellulose, polyvinylpyrrolidone, sodium lauryl sulfate, sodium dioctylsulfosuccinate, gelatin, casein, lecithin (phosphatides), dextran, gum acacia, cholesterol, tragacanth, stearic acid, benzalkonium chloride, calcium stearate, glycerol mono stearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowax 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PV A), 4-(1,1, 3,3-tetramethylbutyl)-phenol polymer with ethylene oxide and formaldehyde (also known as tyloxapol, superione, and triton), poloxamers (e.g., Pluronics F68® and Fl08®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly(glycidol), also known as Olin-10-G® or Surfactant 10-G® (Olin Chemicals, Stamford, Conn.); Crodestas SL-40 (Croda, Inc.); and SA9OHCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-p-D-glucopyranoside; n-heptyl β-D-thioglucoside; n-hexyl β-D-glucopyranoside; nonanoyl-N-methylglucanlide; n-noyl β-D-glucopyranoside; octanoyl-N-methylglucamide; n-octyl-β-D-glucopyranoside; octyl 13-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

In certain embodiments, the surface stabilizer is a poloxamer. Poloxamers can include any type of poloxamer known in the art. Poloxamers are also referred to by the trade name Pluronic®. These two names are used interchangeably, herein. Poloxamers include poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, poloxamer 407, poloxamer 105 benzoate and poloxamer 182 dibenzoate. Poloxamers are also referred to by their trade name Pluronic®. Poloxamers referred to by trade name include Pluronic® 10R5, Pluronic® 17R2, Pluronic® 17R4, Pluronic® 25R2, Pluronic® 25R4, Pluronic® 31R1, Pluronic® F 108 Cast Solid Surfacta, Pluronic® F 108 NF, Pluronic® F 108 Pastille, Pluronic® F 108NF Prill Poloxamer 338, Pluronic® F 127, Pluronic® F 127 NF, Pluronic® F 127 NF 500 BHT Prill, Pluronic® F 127 NF Prill Poloxamer 407, Pluronic® F 38, Pluronic® F 38 Pastille, Pluronic® F 68, Pluronic® F 68 Pastille, Pluronic® F 68 LF Pastille, Pluronic® F 68 NF, Pluronic® F 68 NF Prill Poloxamer 188, Pluronic® F 77, Pluronic® F 77 Micropastille, Pluronic® F 87, Pluronic® F 87 NF, Pluronic® F 87 NF Prill Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 44 NF Poloxamer 124, Pluronic® L 61, Pluronic® L 62, Pluronic® L 62 LF, Pluronic® L 62D, Pluronic® L 64, Pluronic® L 81, Pluronic® L 92, Pluronic® L44 NF INH surfactant Poloxamer 124 View, Pluronic® N 3, Pluronic® P 103, Pluronic® P 104, Pluronic® P 105, Pluronic® P 123 Surfactant, Pluronic® P 65, Pluronic® P 84 and Pluronic® P 85.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG(2000)-Amine Na) (Avanti Polar Lipids, Alabaster, Ala.), Poly(2-methacryloxyethyl trimethylammonium bromide) (Polysciences, Inc., Warrington, Pa.) (also known as S1001), poloxamines such as Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12\text{-}15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($_{C12\text{-}18}$)dimethylbenzyl ammonium chloride, N-alkyl ($C_{12\text{-}14}$)dimethyl-benzyl ammonium chloride, N-tetradecylidmethylbenzyl ammonium chloride monohydrate, dimethyl didecyl ammonium chloride, N-alkyl and ($C_{12\text{-}14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Distearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,Ndialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, Cationic Surfactants: Analytical and Biological Evaluation (Marcel Dekker, 1994); P. and D. Rubingh (Editor), Cationic Surfactants: Physical Chemistry (Marcel Dekker, 1991); and J. Richmond, Cationic Surfactants: Organic Chemistry, (Marcel Dekker, 1990), each of which is incorporated by reference, herein, in its entirety.

Nonpolymeric cationic surface stabilizers are any nonpolymeric compound, such as benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$: (i) none of $R_1$—$R_4$ are $CH_3$; (ii) one of $R_1$—$R_4$ is $CH_3$; (iii) three of $R_1$—$R_4$ are $CH_3$; (iv) all of $R_1$—$R_4$ are $CH_3$; (v) two of $R_1$—$R_4$ are $CH_3$, one of $R_1$—$R_4$ is $C_6H_5CH_2$, and one of $R_1$—$R_4$ is an alkyl chain of seven carbon atoms or less; (vi) two of $R_1$—$R_4$ are CH3, one of $R_1$—$R_4$ is $C_6H_5CH_2$, and one of $R_1$—$R_4$ is an alkyl chain of nineteen carbon atoms or more; (vii) two of $R_1$—$R_4$ are $CH_3$ and one of $R_1$—$R_4$ is the group $C_6H_5$ $(CH_2)n$, where n>1; (viii) two of $R_1$—$R_4$ are $CH_3$, one of $R_1$—$R_4$ is $C_6H_5CH_2$, and one of $R_1$—$R_4$ comprises at least one heteroatom; (ix) two of $R_1$—$R_4$ are $CH_3$, one of $R_1$—$R_4$ is $C_6H_5CH_2$, and one of $R_1$—$R_4$ comprises at least one halogen; (x) two of $R_1$—$R_4$ are $CH_3$, one of $R_1$—$R_4$ is $C_6H_5CH_2$, and one of $R_1$—$R_4$ comprises at least one cyclic fragment; (xi) two of $R_1$—$R_4$ are $CH_3$ and one of $R_1$—$R_4$ is a phenyl ring; or (xii) two of $R_1$—$R_4$ are $CH_3$ and two of $R_1$—$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenanline chloride (Quaternium-15), distearyldimonium chloride (Quaternium-5), dodecyl dimethyl ethylbenzyl ammonium chloride(Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

The surface stabilizers are commercially available and/or can be prepared by techniques known in the art.

3. Pharmaceutical Excipients

Pharmaceutical compositions according to the disclosure may also comprise pharmaceutical excipients. These are one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC®).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorb ate , methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

4. Nanoparticulate Indirubin Particle Size

As used herein, particle size is determined by conventional particle size measuring techniques well known to those skilled in the art. Such techniques include, for example, sedimentation field flow fractionation, photon correlation spectroscopy, light scattering, dynamic light scattering, light diffraction, and disk centrifugation.

The compositions described herein comprise indirubin nanoparticles which have an effective average particle size of less than about 2000 nm, preferably less than about 500 nm, when measured by the above-noted techniques.

If the nanoparticulate indirubin composition additionally comprises one or more non-indirubin nanoparticulate active agents, then such active agents have an effective average particle size of less than about 2000 nm (i.e., 2 microns). In other embodiments, the nanoparticulate non-indirubin active agents can have an effective average particle size of less than about 500 nm, as measured by the above-noted techniques.

By "an effective average particle size of less than about 2000 nm" it is meant that at least 50% of the nanoparticulate indirubin particles or nanoparticulate non-indirubin active agent particles have an average particle size of less than about 2000 nm, when measured by the above-noted techniques. In other embodiments, at least about 70%, at least about 90%, at least about 95%, or at least about 99% of the nanoparticulate indirubin particles or nanoparticulate non-indirubin active agent particles have a particle size of less than the effective average, by weight, i.e., less than about 2000 nm.

If the nanoparticulate indirubin composition is combined with a conventional or microparticulate indirubin composition or non-indirubin active agent composition, then such a composition is either solubilized or has an effective average particle size of greater than about 2 microns. By "an effective average particle size of greater than about 2 microns" it is meant that at least 50% of the conventional indirubin or conventional non-indirubin active agent particles have a particle size of greater than about 2 microns, by weight, when measured by the above-noted techniques. In other embodiments, at least about 70%, about 90%, about 95%, or about 99%, by weight, of the conventional indirubin or conventional non-indirubin active agent particles have a particle size greater than about 2 microns.

In the present disclosure, the value for D50 of a nanoparticulate indirubin composition is the particle size below which 50% of the indirubin particles fall, by weight. Similarly, D90 is the particle size below which 90% of the indirubin particles fall, by weight.

5. Concentration of Nanoparticulate Indirubin and Surface Stabilizers

The relative amounts of indirubin and one or more surface stabilizers can vary widely. The optimal amount of the individual components can depend, for example, upon the hydrophilic lipophilic balance (HLB), melting point, and the surface tension of water solutions of the stabilizer, etc.

The relative amount of indirubin can vary from about 99.5% to about 0.001%, from about 95% to about 0.1%, or from about 90% to about 0.5%, by weight, based on the total combined dry weight of the indirubin and at least one surface stabilizer, not including other excipients. In specific embodiments, the relative amount of indirubin can vary from 99.999% to 80%, from 99.99% to 80%; from 99.9% to 80%; from 99% to 80%; from 98% to 80%; from 97% to 80%; from 96% to 80%; from 95% to 80%; from 94% to 80% from 93% to 80%; from 92% to 80%; from 91% to 80%; or from 90% to 80%, by weight, based on the total combined dry weight of the indirubin and at least one surface stabilizer, not including other excipients.

The relative amount of the at least one surface stabilizer can vary from about 0.0001% to about 99.999%, from about 5.0% to about 99.9%, or from about 10% to about 99.5%, by weight, based on the total combined dry weight of the indirubin and at least one surface stabilizer, not including other excipients. In specific embodiments, the relative amount of the at least one surface stabilizer can vary from 0.000001% to 20%, from 0.00001% to 20%; from 0.0001% to 20%; from 0.001% to 20%; from 0.01% to 20%; from 0.1% to 20%; from 1% to 20%; from 2% to 20%; from 3% to 20% from 4% to 20%; from 5% to 20%; or from 10% to 20%, by weight, based on the total combined dry weight of the indirubin and at least one surface stabilizer, not including other excipients.

Methods of Making Nanoparticulate Indirubin Formulations

The nanoparticulate indirubin compositions can be made using, for example, milling, emulsification, or precipitation techniques.

Following milling, emulsification, precipitation, etc., the resultant nanoparticulate indirubin compositions can be utilized in solid or liquid dosage formulations, such as controlled release formulations, solid dose fast melt formulations, aerosol formulations, nasal formulations, lyophilized formulations, tablets, capsules, solid lozenge, powders, creams, ointments, etc.

1. Milling to Obtain Nanoparticulate Indirubin Dispersions

Milling indirubin to obtain a nanoparticulate dispersion comprises dispersing indirubin particles in a liquid dispersion media in which indirubin is poorly soluble, followed by applying mechanical means in the presence of grinding media to reduce the particle size of indirubin to the desired effective average particle size. The dispersion media can be, for example, water, safflower oil, ethanol, t-butanol, glycerin, polyethylene glycol (PEG), hexane, or glycol.

The indirubin particles can be reduced in size in the presence of at least one surface stabilizer. Alternatively, the indirubin particles can be contacted with one or more surface stabilizers after attrition. Other compounds, such as a diluent, can be added to the indirubin/surface stabilizer composition during the size reduction process. Dispersions can be manufactured continuously or in a batch mode.

2. Precipitation to Obtain Nanoparticulate Indirubin Compositions

Another method of forming the desired nanoparticulate indirubin composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving indirubin in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

3. Emulsification to Obtain Indirubin Nanoparticulate Compositions

Such a method comprises 1) dissolving indirubin in a solvent; 2) emulsifying the indirubin solution in a second liquid in which indirubin is poorly soluble; 3) removing the solvent to solidify the indirubin nanoparticles. Typically said solvent is not miscible with the dispersion media. The dispersion media can be, for example, water, safflower oil, ethanol, t-butanol, glycerin, polyethylene glycol (PEG), hexane, or glycol.

The indirubin particles can be reduced in size in the presence of at least one surface stabilizer. Alternatively, the indirubin particles can be contacted with one or more surface stabilizers either before or after attrition. Other compounds, such as a diluent, can be added to the indirubin/surface stabilizer composition either before, during, or after the size reduction process. Dispersions can be manufactured continuously or in a batch mode.

Methods of Using Nanoparticulate Indirubin Formulations Described herein

1. Applications of the Nanoparticulate Compositions

The nanoparticulate indirubin compositions described herein may be used to treat cancer. The nanoparticulate indirubin compositions described herein may also be used to treat leukemia, especially chronic myelogenous leukemia (CML) and glioblastomas. The nanoparticulate indirubin compositions described herein may be used to treat inflammatory diseases including psoriasis. The nanoparticulate indirubin compositions described herein may be used to treat neurodegenerative disorders including Alzheimer's disease 2. Dosage Forms The nanoparticulate indirubin compositions described herein can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably. The nanoparticulate indirubin compositions described herein can also be administered to the central nervous system, e.g., to the brain or spinal cord. In certain embodiments, the nanoparticulate indirubin compositions described herein are administered to the brain. According to certain embodiments, the nanoparticulate indirubin compositions described herein are administered with an agent that enhances the permeability of the blood brain barrier (BBB) to nanoparticulate indirubin compositions.

Moreover, the nanoparticulate indirubin compositions described herein can be formulated into any suitable dosage form, including but not limited to liquid dispersions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

Nanoparticulate indirubin compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate indirubin compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffeting agents.

Liquid nanoparticulate indirubin dosage forms for oral administration include pharmaceutically acceptable emulsions, solutions, suspensions, syrups, and elixirs. In addition to indirubin, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

The following examples are given for illustrative purposes. It should be understood, however, that the nanoparticulate indirubin composition described herein are not to be limited to the specific conditions or details described in these examples. Throughout the specification, any and all references to a publicly available document, including a U.S. patent, are specifically incorporated by reference.

In the examples that follow, the value for D50 is the particle size below which 50% of the indirubin particles fall. Similarly, D90 is the particle size below which 90% of the indirubin particles fall.

The formulations in the examples that follow were also investigated using a light microscope. Here, "stable" nanoparticulate dispersions (uniform Brownian motion) were readily distinguishable from "aggregated" dispersions (relatively large, nonuniform particles without motion). Stable, as known in the art and used herein, means the particles don't substantially aggregate or ripen (increase in fundamental particle size).

EXAMPLES

Example 1

Preparation of a Nanoparticulate Dispersion of Indirubin 5.6 mg of indirubin was dissolved in 1 ml dimethyl sulfoxide (DMSO). The indirubin/DMSO solution was then added dropwise to a beaker containing 30 ml of 1% by weight Pluronic F-68® (poloxamer 188) while stirring. The resulting indirubin nanoparticles were purified by dialysis.

Particle size analysis was performed with a Malvern particle size analyzer (Worcestershire, UK). The average particle size was found to be 616.3 nm.

Example 2

Preparation of a Nanoparticulate Dispersion of Indirubin 22.4 mg of indirubin was dissolved in 4 ml dimethyl sulfoxide (DMSO). The indirubin/DMSO solution was then added dropwise to a beaker containing 200 ml of 2% by weight Pluronic F-68® (poloxanler 188) while stirring. The resulting indirubin nanoparticles were purified by dialysis.

Particle size analysis was performed with a Malvern particle size analyzer (Worcestershire, UK). The average particle size was found to be 457.9 nm.

Example 3

Preparation of a Nanoparticulate Powder of Indirubin 100.0 mg of indirubin was dissolved in 4 ml methylene chloride. The resulting solution was mixed with 100 ml of 2% by weight Pluronic F-68® (poloxamer 188) and the mixture was homogenized with an IKA homogenizer at 24000 rpm for 30 seconds to generate a fine emulsion. The emulsion was then transferred to a beaker and stirred magnetically at approximately 500 rpm for 4 hours to remove the methylene chloride. Such prepared nanoparticle suspension was further concentrated with a tangential flow filtration device to approximately 5 mi. The concentrated particle suspension was lyophilized.

Particle size analysis was performed with a Malvern particle size analyzer (Worcestershire, UK). The average particle size was found to be 259.3 nm.

Example 4

Indirubin Animal Study

The retroviral constructs MSCV-GFP, or MSCV-BCR-ABL-GFP carrying the BCR-ABL cDNA were used to make high titer, helper-free, replication-defective ecotropic viral stocks by transient transfection of 293T cells by use of the kat system. Then, 6- to 10-week-old wild-type C57BL/6 (The Jackson Laboratory) mice were used for leukemogenesis experiments. In brief, to induce CML, bone marrow cells from 5-FU-treated (200 mg/kg) donor mice were transduced twice with BCR-Abbott Biotechnology Ltd. retrovirus by cosedentation in the presence of interleukin-3, interleukin-6, and stem cell factor. Wild-type recipient mice were prepared by 1100 cGy gamma irradiation. A dose of $0.5 \times 10^6$ cells was transplanted via tail vein injection. Diseased mice were analyzed by histopathologic and biochemical analyses.

In this experiment, three mice, Mouse #1, 2 and 3, were tested. Four weeks after the injection, Mouse #2 was fed with 0.1 ml of the nanoparticle indirubin suspension prepared in Example 2 (20 mg/ml) followed by another dose two days later, Mouse #3 was fed with 0.3 ml of the same suspension followed by another dose two days later. Mouse #1 was used as a control without the indirubin nanoparticles being fed. It was observed that Mouse #1 died 5 weeks after administration of the drug to mice #2 and #3, whereas Mouse #2 survived 8 weeks and Mouse #3 survived 9 weeks.

What is claimed is:

1. A method of treating cancer in a subject in need thereof comprising administering an effective amount of the nanoparticulate indirubin composition comprising (a) particles of indirubin or an indirubin derivative selected from the group consisting of: mesoindigo, indirubin-3'-oxime, 5'-nitro-indirubinoxime, 5'-fluoro-indirubinoxime, 5'-bromo-indirubin-3'-monoxime, 6'-bromo-indirubin-3'-monoxime, 7'-bromo-indirubin-3'-monoxime, 5'-trimethylacetamino-indirubinoxime, IDR-E804, and an indirubin hydrazone derivative, wherein the particles have an effective average particle size of less than 2 microns; and (b) at least one surface stabilizer comprising poloxamer 188; and wherein said cancer is glioblastoma, leukemia, head and neck cancer, or a cancer treatable by inhibiting a cyclin-dependent kinase.

2. The method of claim 1, wherein the cancer is glioblastoma multiforme, or wherein the leukemia is CML (Chronic Myeloid Leukemia).

3. The method of claim 1, wherein said subject is a human.

4. The method of claim 1, further comprising administering at least one non-indirubin active agent.

5. The method of claim 1, wherein at least about 70% of the indirubin particles have a particle size less than the effective average particle size.

6. The method of claim 1, wherein the composition is formulated for oral or intravenous administration.

7. The method of claim 1, wherein the composition further comprises one or more pharmaceutically acceptable excipients, carriers, or a combination thereof.

* * * * *